(12) United States Patent
Narendranath et al.

(10) Patent No.: US 9,034,631 B2
(45) Date of Patent: May 19, 2015

(54) SYSTEMS AND METHODS FOR YEAST PROPAGATION

(71) Applicant: POET Research Inc., Sioux Falls, SD (US)

(72) Inventors: Neelakantam V. Narendranath, Sioux Falls, SD (US); Stephen M. Lewis, Sioux Falls, SD (US)

(73) Assignee: Poet Research, Inc., Sioux Falls, SD (US)

( * ) Notice: Subject to any disclaimer, the term of this patent is extended or adjusted under 35 U.S.C. 154(b) by 14 days.

(21) Appl. No.: 13/804,364

(22) Filed: Mar. 14, 2013

(65) Prior Publication Data

US 2014/0273167 A1 Sep. 18, 2014

(51) Int. Cl.
| C12N 1/00 | (2006.01) |
| C12M 1/00 | (2006.01) |
| C12N 1/16 | (2006.01) |
| C12N 1/18 | (2006.01) |

(52) U.S. Cl.
CPC ............ *C12M 45/09* (2013.01); *C12N 1/16* (2013.01); *C12N 1/18* (2013.01)

(58) Field of Classification Search
CPC ............ C12N 15/81; C12N 1/18; C12M 1/00
USPC ......................................... 435/254.21, 289.1
See application file for complete search history.

(56) References Cited

U.S. PATENT DOCUMENTS

| 4,530,846 | A |   | 7/1985  | Nagodawithana et al. |
| 5,424,417 | A |   | 6/1995  | Torget et al. |
| 6,022,419 | A |   | 2/2000  | Torget et al. |
| 6,159,724 | A | * | 12/2000 | Ehret ........................ 435/252.1 |
| 7,344,876 | B2 |  | 3/2008  | Levine |
| 7,622,284 | B2 |  | 11/2009 | Op Den Camp et al. |
| 7,820,418 | B2 |  | 10/2010 | Karl et al. |
| 7,968,320 | B2 | * | 6/2011 | Degre et al. ................... 435/161 |
| 8,105,801 | B2 | * | 1/2012 | Nielsen et al. .................. 435/41 |
| 8,450,094 | B1 |  | 5/2013 | Narendranath et al. |
| 8,815,552 | B2 |  | 8/2014 | Narendranath et al. |
| 2004/0058429 | A1 |  | 3/2004 | Bill et al. |
| 2004/0234649 | A1 |  | 11/2004 | Lewis et al. |
| 2006/0051847 | A1 |  | 3/2006 | Gunnarsson et al. |
| 2006/0246563 | A1 |  | 11/2006 | Eroma et al. |
| 2009/0093027 | A1 |  | 4/2009 | Balan et al. |
| 2009/0325241 | A1 |  | 12/2009 | Jeffries et al. |
| 2010/0124759 | A1 |  | 5/2010 | Wang et al. |
| 2010/0159552 | A1 |  | 6/2010 | Benson et al. |
| 2010/0196994 | A1 |  | 8/2010 | van Leeuwen et al. |
| 2010/0227369 | A1 |  | 9/2010 | Narendranath et al. |
| 2011/0262983 | A1 |  | 10/2011 | Jeffries et al. |
| 2011/0269202 | A1 |  | 11/2011 | Taron et al. |
| 2012/0309069 | A1 |  | 12/2012 | Bell et al. |
| 2014/0065700 | A1 |  | 3/2014 | Narendranath et al. |
| 2014/0273166 | A1 |  | 9/2014 | Narendranath |

FOREIGN PATENT DOCUMENTS

| WO | WO 2011/159915 | 12/2011 |
| WO | WO 2012/100187 | 7/2012 |
| WO | WO 2012/125739 | 9/2012 |

OTHER PUBLICATIONS

Aiba et al., Fed batch culture of *Saccharomyces cerevisiae*: a perspective of computer control to enhance the productivity in baker's yeast cultivation. Biotechnology and Bioengineering, vol. 28 (1976) pp. 1001-1016.*
Soni et al., A solid state fermentation based bacterial alpha-amylase and fungal glucoamylase system and its suitability for the hydrolysis of wheat starch. Process Biochemistry, VOl. 39 (2003) pp. 185-192.*
U.S. Appl. No. 14/465,177, filed Aug. 2014, Narendranath et al.
Jeffries, T.W. et al. "Fermentation of Hemicellulosic Sugars and Sugar Mixtures by *Candida shehatae* ", Biotechnology and Bioengineering 31, (1988), pp. 502-506.

* cited by examiner

*Primary Examiner* — Jon P Weber
*Assistant Examiner* — Kara Johnson
(74) *Attorney, Agent, or Firm* — Kagan Binder, PLLC

(57) ABSTRACT

The present invention relates to systems and methods for propagating yeast using a feedstock material such as starch and one or more enzymes (e.g., an enzyme cocktail) to break down the feedstock material into one or more monosaccharides at a sufficient rate so that the yeast can use the monosaccharides as a carbon source for producing more yeast cells while not producing an undue amount of alcohol.

15 Claims, 8 Drawing Sheets

Sugars, organic acids and ethanol after 24 hours of aerobic growth
of *S. cerevisiae* in starch based medium

| Time (h) | Maltose (% w/v) | Glucose (% w/v) | Lactic acid (ppm) | Acetic acid (ppm) | Ethanol (% v/v) | Glycerol (% w/v) |
|---|---|---|---|---|---|---|
| 0 | 0.10 | 0.276 | 719.283 | 214.207 | 0.11 | 0.553 |
| 6 | 0.07 | 0.022 | 701.436 | 211.126 | 0.89 | 0.57 |
| 24 | 0.00 | 0.005 | ND | ND | 0.01 | 0.01 |

TABLE 1

FIGURE 5A

Sugars, organic acids and ethanol after 24 hours of incubation of
starch based medium

| Time (h) | Maltose (% w/v) | Glucose (% w/v) | Lactic acid (ppm) | Acetic acid (ppm) | Ethanol (% v/v) | Glycerol (% w/v) |
|---|---|---|---|---|---|---|
| 0 | 0.10 | 0.27 | 705.77 | 222.328 | 0.05 | 0.546 |
| 6 | 0.09 | 1.541 | 729.008 | 201.166 | 0.05 | 0.55 |
| 24 | 0.08 | 2.168 | 735.03 | 94.267 | 0.09 | 0.56 |

TABLE 2

FIGURE 5B

Sugars, organic acids and ethanol after 24 hours of aerobic growth
of modified *S. cerevisiae* in starch based medium

| Time (h) | Maltose (% w/v) | Glucose (% w/v) | Lactic acid (ppm) | Acetic acid (ppm) | Ethanol (% v/v) | Glycerol (% w/v) |
|---|---|---|---|---|---|---|
| 0 | 0.09 | 0.346 | 446.196 | 217.639 | 0.06 | 0.487 |
| 6 | 0.06 | 0.242 | 461.507 | 242.191 | 0.75 | 0.50 |
| 24 | 0.01 | 0.007 | 39.853 | 26.637 | 0.01 | 0.01 |

TABLE 3

FIGURE 6A

Sugars, organic acids and ethanol after 24 hours of aerobic growth
of non-modified *S. cerevisiae* in starch based medium

| Time (h) | Maltose (% w/v) | Glucose (% w/v) | Lactic acid (ppm) | Acetic acid (ppm) | Ethanol (% v/v) | Glycerol (% w/v) |
|---|---|---|---|---|---|---|
| 0 | 0.09 | 0.356 | 447.575 | 216.911 | 0.01 | 0.489 |
| 6 | 0.07 | 1.194 | 451.015 | 172.904 | 0.19 | 0.50 |
| 24 | 0.01 | 0.007 | 47.746 | 33.221 | 0.01 | 0.01 |

TABLE 4

FIGURE 6B

Sugars, organic acids and ethanol after 24 hours of aerobic growth
of *S. cerevisiae* in starch based medium

| Time (h) | Maltose (% w/v) | Glucose (% w/v) | Lactic acid (ppm) | Acetic acid (ppm) | Ethanol (% v/v) | Glycerol (% w/v) |
|---|---|---|---|---|---|---|
| 0 | 0.22 | 0.173 | 524.912 | 232.386 | 0.06 | 0.556 |
| 5.5 | 0.05 | 1.429 | 455.891 | 204.152 | 0.71 | 0.55 |
| 21 | 0.01 | ND | 45.043 | 69.374 | 1.63 | 0.15 |
| 24 | 0.01 | ND | 65.925 | 87.183 | 1.34 | 0.06 |

TABLE 5

FIGURE 7A

Glucose, organic acids and ethanol after 24 hours of aerobic growth
of *S. cerevisiae* in glucose based medium

| Time (h) | Glucose (% w/v) | Lactic acid (ppm) | Acetic acid (ppm) | Ethanol (% v/v) | Glycerol (% w/v) |
|---|---|---|---|---|---|
| 0 | 6.138 | 404.576 | 170.39 | 0.04 | 0.477 |
| 5.5 | 4.8 | 413.131 | 224.094 | 0.80 | 0.52 |
| 21 | 0.007 | 26.556 | 73.778 | 1.658 | 0.205 |
| 24 | ND | 33.948 | 73.793 | 1.30 | 0.119 |

TABLE 6

FIGURE 7B

SYSTEMS AND METHODS FOR YEAST PROPAGATION

FIELD OF INVENTION

The present invention relates to growing yeast such as *Saccharomyces cerevisiae*. More particularly, the present invention relates to growing yeast using a feedstock material such as starch and one or more enzymes (e.g., an enzyme cocktail).

BACKGROUND

Ethanol producers often purchase yeast for fermentation from a yeast supplier (e.g., in dried form, and/or as a cream liquid suspension). Yeast can constitute a large operational cost for many ethanol producers, and as such many ethanol producers add a bare minimum of yeast to fermentation processes.

However, there may be a number of benefits to increasing yeast loading within a fermentation. For example, one substantial benefit can be a reduced time period for fermentation, thereby effectively increasing the output for a given ethanol producing facility. Another major benefit of increased yeast loading can be a reduction in losses relating to lactic bacteria contamination. A higher yeast loading can mean that contaminants cannot compete with the dominant yeast population, thus ensuring a cleaner operation. Unfortunately, given the cost of yeast, increased inoculation of fermentations is often cost prohibitive.

If ethanol production facilities could grow their own yeast in a cost effective manner, then larger doses of yeast could be added to the fermenters. This can result in multiple benefits, including reduced yeast costs, faster fermentation (effectively increasing plant capacity), and/or reduced microbial contamination risks (due to out-competition of lactic bacteria by the larger yeast population).

However, growing (propagating) yeast such as, e.g., *Saccharomyces cerevisiae* can be challenging. For example, if the yeast is grown in too high a concentration of glucose, the yeast can switch over from aerobic metabolic pathways to ethanol producing anaerobic metabolism, even under highly aerated conditions. This shift, when propagating yeast is generally not desirable if the purpose is to generate substantial numbers of yeast cells. Even under highly aerated conditions, if the glucose concentration in a propagation medium exceeds about 5 g/L, the yeast, *S. cerevisiae*, can sometimes begin to make ethanol (fermentative pathway). This is known as the "Crabtree" effect (suppression of respiration by high glucose). Likewise, when not enough oxygen is present, metabolism may shift to the fermentative pathway.

To help avoid the Crabtree Effect, *Saccharomyces cerevisiae* yeast is often grown by yeast suppliers in well aerated yeast propagation tanks with tightly monitored glucose feed (typically molasses feedstock is used in a fed-batch process) to help ensure that glucose levels remain low enough that metabolism remains aerobic.

Unfortunately, for the vast majority of ethanol producers, maintaining the conditions necessary to grow their own yeast can be economically and/or technically infeasible. The equipment and technical expertise required to generate yeast in appreciable volumes is often too great a risk and cost, and as such they must often rely upon yeast suppliers. For example, careful metering of the glucose stream by an ethanol producer can be technically difficult due to large batch-to-batch variation in molasses, and raises a major risk if done improperly due to facility shutdowns associated with a shortage of yeast.

Further, molasses is not typically utilized in an ethanol production facility the United States (North America), and the logistics required to have molasses delivered would often be a major hurdle to growing yeast by an ethanol producer.

It would be advantageous to provide for alternative systems and methods to propagate yeast, e.g., systems and methods that do not require stringent molasses metering systems. Such systems and methods could allow for more preferred yeast dosing in ethanol fermentations.

SUMMARY OF INVENTION

The present invention relates to growing yeast using a feedstock material and one or more enzymes (e.g., an enzyme cocktail) that can break down polysaccharide(s) and/or oligosaccharide(s) in the feedstock material into one or more monosaccharides at a sufficient rate so that the yeast can use the monosaccharides as a carbon source for producing more yeast cells while not producing an undue amount of alcohol. By selecting the types and amounts of feedstock material(s) and types and amounts of enzyme(s), monosaccharides can be generated at a desired rate.

Providing monosaccharides in such a manner can be relatively simple, robust, and easy. For example, yeast propagation according to the present invention can be performed according to a simple batch process, and a fed-batch process is not required.

Also, many ethanol production facilities, especially those that use starch to make ethanol, can grow their own yeast populations according to the systems and methods of the present invention, and often without incurring substantial added costs. Using the systems and methods according to the present invention has the potential to effectively reduce overall cost of ethanol for the fuel industry, and eventually be able to assist in other bio-products that may be generated using yeasts, especially modified yeasts.

Additionally, in some embodiments, systems and methods according to the present invention may permit ethanol producers to generate yeast cultures on-site at a significantly reduced cost. This may allow not only monetary savings, but also the ability for ethanol producers to increase yeast loading in fermentation in order to increase yields, decrease risk of microbial contamination, condition the production yeast to the production medium, and/or condition amylolytic enzyme expressing yeast such as *Saccharomyces cerevisiae* yeast to generate enzymes tailored to the feedstock being used for ethanol production.

According to one aspect of the present invention, a method of propagating yeast includes:
  providing a composition including:
    a propagation medium including:
      a nutrient source;
      a carbon source comprising a feedstock material having one or more polysaccharides and/or one or more oligosaccharides; and
      one or more enzymes that can convert at least a portion of the one or more polysaccharides and/or one or more oligosaccharides into one or more monosaccharides; and
    a first cell mass of the yeast, wherein the yeast can use at least a portion of the one or more monosaccharides to grow the first cell mass of the yeast for a time period to form a second cell mass of the yeast; and
  growing the first cell mass of yeast for a time period to form a second cell mass of yeast that is greater than the first cell mass of yeast.

According to another aspect of the present invention, a system for propagating yeast includes:
a propagation reactor vessel including a composition having:
a propagation medium including:
a nutrient source;
a carbon source including a feedstock material having one or more polysaccharides and/or one or more oligosaccharides; and
one or more enzymes that can convert at least a portion of the one or more polysaccharides and/or one or more oligosaccharides into one more monosaccharides; and
a first cell mass of the yeast, wherein the yeast can use at least a portion of the one or more monosaccharides to grow the first cell mass of the yeast for a time period to form a second cell mass of the yeast that is greater than the first cell mass of yeast; and
an aerator coupled to the propagation reactor vessel to aerate the composition.

In preferred embodiments, the one or more enzymes include glucoamylase and/or fungal alpha-amylase.

In preferred embodiments, the one or more polysaccharides and/or one or more oligosaccharides include starch material such as corn flour.

BRIEF DESCRIPTION OF THE DRAWINGS

FIG. 5A shows Table 1 from Example 1.
FIG. 5B shows Table 2 from Example 1.
FIG. 6A shows Table 3 from Example 2.
FIG. 6B shows Table 4 from Example 2.
FIG. 7A shows Table 5 from Example 3.
FIG. 7B shows Table 6 from Example 3.

DETAILED DESCRIPTION

Figure 1:
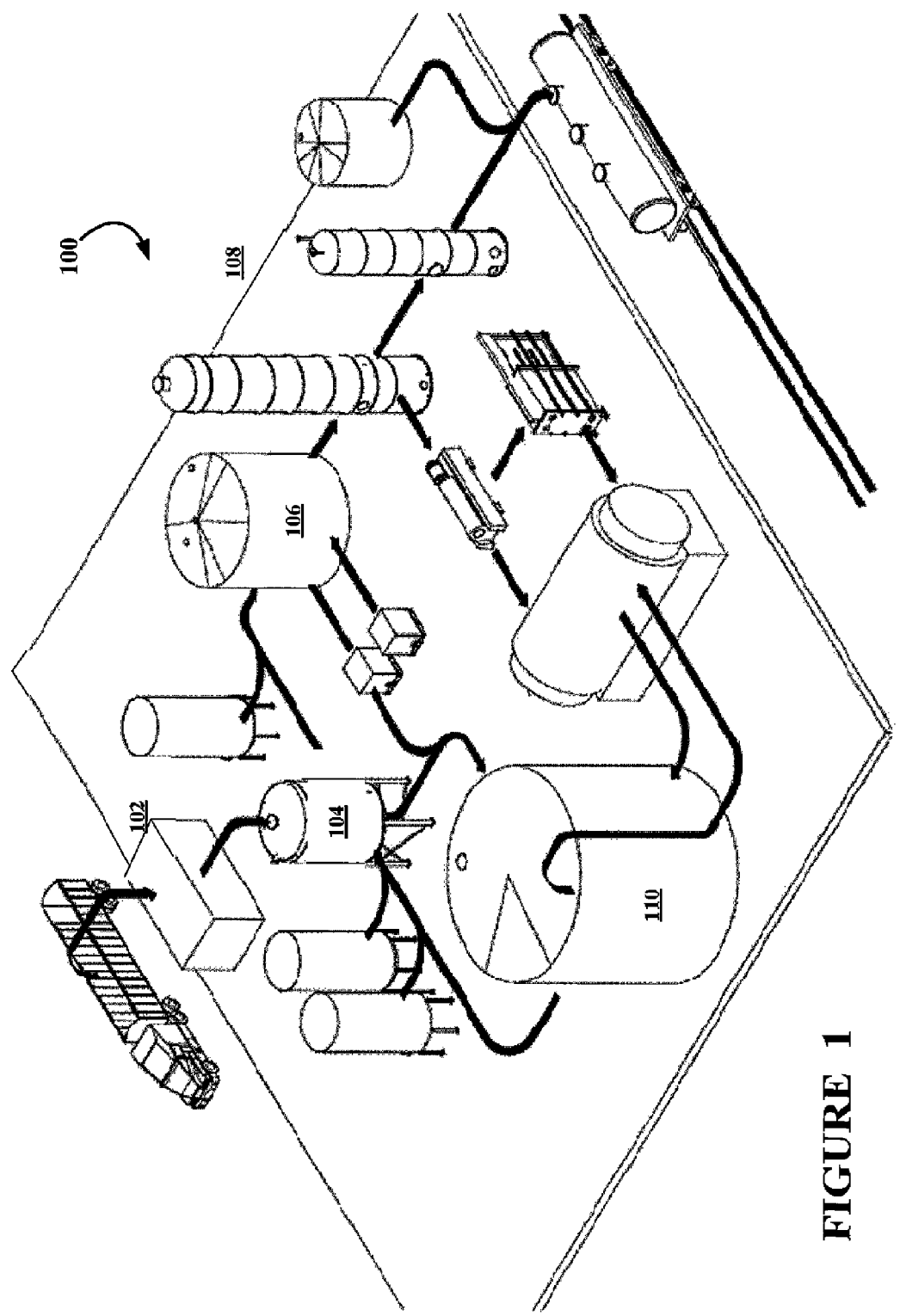
FIG. 1 shows a perspective view of a biorefinery including an ethanol production facility.

The present invention will now be described in detail with reference to several embodiments thereof and as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Propagating yeast according to the present invention includes providing a composition including a propagation medium and a first cell mass of the yeast.

A propagation medium for propagating yeast generally includes at least a nutrient source, a carbon source, and water to form a medium that can facilitate growth of a sufficient amount of yeast cell mass for inoculation to a fermentation system. The initial cell mass of yeast can be included either while the medium is being formed, after the medium is formed, or both.

Exemplary ingredients that can be included in the nutrient source include one or more of yeast extract, urea, diammonium phosphate, magnesium sulfate, zinc sulfate or other salts, and the like.

In addition to a nutrient source, a propagation medium according to the present invention also includes a carbon source that includes a feedstock material, and one or more enzymes.

At least a portion of the feedstock material includes one or more polysaccharides and/or one or more oligosaccharides. The one or more polysaccharides and/or one or more oligosaccharides can be broken down (e.g., via enzymatic hydrolysis) into one or more monosaccharides during propagation and function as a carbon source for the yeast to produce more yeast cells. Exemplary polysaccharides and/or oligosaccharides include those that can be broken down into C6 monosaccharides. In a preferred embodiment, a polysaccharide includes starch and a corresponding monosaccharide includes glucose.

Exemplary feedstock materials can be prepared from one or more grains such as corn, soybean, sorghum/milo, barley, wheat, etc., or a combination of such grains. In some embodiments, feedstock material is preferably prepared from whole grain corn or one or more portions of fractionated corn.

Raw feedstock such as corn grains is preferably prepared to make the feedstock material accessible by the one or more enzymes so that the enzymes can break down the polysaccharides and/or oligosaccharides to one or more monosaccharides at a desired rate. As discussed herein, a desired rate of monosaccharide (e.g., glucose) production includes a rate that produces enough glucose to propagate yeast within a desired time period (e.g., 24 hours) yet avoids the production of an undue amount of ethanol via the Crabtree effect. A desired rate hydrolyzing polysaccharides and/or oligosaccharides in a feedstock material to one or more monosaccharides may include a rate that mimics rates conventionally used to manually feed glucose containing material (e.g., molasses) in a fed-batch propagation system. Exemplary methods of preparing feedstock material for use in a propagation medium according to the present invention include those used to prepare feedstock for enzymatic hydrolysis in ethanol processes discussed below in connection with preparation system 204 in FIGS. 2A and 2B (e.g., milling).

In some embodiments, the feedstock material includes one or more of corn flour, milled corn endosperm, sorghum flour, soybean flour, wheat flour, biomass derived starch, and barley flour.

The feedstock material can be included in any amount that provides a sufficient amount of monosaccharide (e.g., glucose) via enzymatic hydrolysis as described herein to support a desired amount of yeast growth within a desired time period. Exemplary amounts of feedstock material that can be included in a propagation medium that can support producing enough yeast within about 12-48 hours for a commercial ethanol fermentation system include starch in a range of from 15-75 grams dry flour per liter of propagation medium.

In addition to a feedstock material as described herein, a propagation medium according to the present invention includes one or more enzymes that can convert at least a portion of the one or more polysaccharides and/or one or more oligosaccharides into one or more monosaccharides via hydrolysis and function as a carbon source for supporting reproduction of yeast cells. The speed of hydrolysis is dependent upon factors such as enzyme loading levels, enzyme activity, and the pH and temperature of the propagation medium. In preferred embodiments, the one or more enzymes include one or more amylolytic enzymes. Exemplary amylolytic enzymes include one or more of alpha-amylase (e.g., fungal alpha-amylase), glucoamylase, other amylases, and amyloglucosidases.

In some embodiments, the one or more enzymes may include glucoamylase present in an amount in the range from 0.25 to 30 glucoamylase units (AGUs) per gram of dry solids in the propagation medium (preferably from 0.75 to 30 glucoamylase units (AGUs) per gram of dry solids in the propagation medium); fungal alpha-amylase present in an amount in the range from 0.03 to 4 fungal alpha-amylase units (FAU-F) per gram of dry solids in the propagation medium (preferably from 0.05 to 4 fungal alpha-amylase units (FAU-F) per gram of dry solids in the propagation medium); and combinations thereof. Enzymes such as these that can degrade feedstock material according to the present invention are well known and can be commercially obtained from, e.g., Novozymes®, Bagsvaerd Denmark.

Optionally, one or more additional enzymes may be included in a propagation medium such as proteases, phytases, cellulases and hemicellulases, as may be desired for any particular yeast propagation (typically dependent upon the feedstock/starch supply being utilized).

Optional additional agents for propagating yeast are well known and include, e.g., agents supplied with yeast such as antibiotics, supplemental or accessory enzymes, materials for adjusting and maintaining pH, nutrients or other components providing nutritional or other benefits to the yeast.

The propagation methods described herein may be desirable for growing many types of yeasts. In many embodiments, the yeast includes a yeast that could benefit from being propagated in a medium that introduces a carbon source such as glucose in a relatively controlled manner via enzymatic hydrolysis of a feedstock material so that the yeast can reproduce yet not produce an undue amount of alcohol via fermentation (e.g., suppression of respiration due to the Crabtree effect). Exemplary yeast include *Saccharomyces cerevisiae* that can propagate using at least glucose as a carbon source. In some embodiments, the yeast can include non-genetically modified yeast such as non-genetically modified *Saccharomyces cerevisiae*. In other embodiments, the yeast can include genetically modified yeast such as genetically modified recombinant *Saccharomyces cerevisiae*.

Yeast can be introduced into the propagation in any initial amount. Typically, the initial amount is determined based on considerations such as the desired time period for completing propagation and the desired cell count at the end of propagation, the nutrient source, the carbon source including the feedstock material, the enzyme(s), temperature, pH, and the like. In some embodiments, the yeast is provided to the propagation medium in an amount in the range from 0.01 to 10 grams dry yeast per liter of the propagation medium, preferably in an amount in the range from 0.02 to 5 grams dry yeast per liter of the propagation medium.

As mentioned, a method of propagating yeast according to the present invention includes providing a composition that includes a propagation medium and a first cell mass of yeast; and then growing the first cell mass of yeast for a time period to form a second cell mass of yeast that is greater than the first cell mass of yeast.

According to the present invention, the types and amounts of the one or more enzymes and feedstock material are selected so that the enzymes break down the polysaccharides and/or oligosaccharides of the feedstock material via enzymatic hydrolysis into monosaccharides so that the monosaccharides (e.g., glucose) are introduced as a carbon source for the yeast in a relatively controlled manner so that the yeast can reproduce in a desired time period yet not produce an undue amount of alcohol via fermentation (e.g., suppression of respiration due to the Crabtree effect).

Preferably, the one or more enzymes are present in an amount and the feedstock material is present in an amount so that substantially no ethanol is produced by the yeast during at least a portion of the time period. Preferably, substantially no ethanol is produced by the yeast during the entire growing time period. As used herein, "substantially no ethanol" means that the level of ethanol produced is 1 percent v/v or less, preferably 0.5 percent v/v or less, preferably 0.05 percent v/v or less.

Preferably, the one or more enzymes are present in an amount and the feedstock material is present in an amount to produce one or more monosaccharides in an amount to grow a second cell mass of yeast within a desired time period. For example, a target monosaccharide production rate can include producing glucose in an amount in a range from 0.1 to 5 percent w/v within a 24 hour time period, preferably in a range from 0.5 to 3 percent w/v within a 24 hour time period. Preferably, the amount of glucose produced within a 24 hour time period is less than 75 g/L, preferably 30 g/L or less.

Other conditions can also be selected to promote desired yeast growth such as temperature of the propagation medium, oxygen level of the propagation medium (aeration), agitation/stirring conditions, pH of the propagation medium, and the like.

At least a portion of the propagation time period, and preferably the entire propagation time period, is performed while sufficient oxygen is present so that the yeast produce more yeast via aerobic respiration and do not produce an undue amount of alcohol (e.g., ethanol) via an anaerobic fermentative pathway. A suitable amount of oxygen for respiration is well known and can be provided in a propagation reactor vessel by any well known aerator apparatus such as an air sparging system.

Further, sufficient aeration can be promoted by agitating the propagation medium. Agitation is well known and can be provided by, e.g., mechanical stirring.

The temperature and/or the pH of the propagation medium can be any temperature that permits the contents of the propagation medium to function properly such as permitting the enzymes to break down the feedstock material into sugars and the yeast to reproduce. Exemplary temperatures include a temperature in the range from 15° C. to 50° C., preferably from 20° C. to 40° C., and even more preferably from 25° C. to 37° C. Exemplary pH values include a pH in the range from 2-8, preferably from 3 to 7.5, and even more preferably from 3.5 to 6.5.

Once the yeast is present in the propagation medium, the yeast can grow for any desired time period. Typically, the yeast will be grown under conditions to provide a sufficient amount of yeast cells to perform ethanol production via fermentation. Also, the yeast cells are typically grown for an economically efficient time period. Exemplary time periods include from 30 minutes to 72 hours, preferably from 10 to 48 hours, and even more preferably from 12 to 24 hours.

By propagating yeast in a manner described herein, the enzymes may interact with the feedstock material such as starch in order to hydrolyze a sufficient quantity of starch, yet not too much, into glucose within a desired time period. Further, the conditions described herein may be controlled in order to ensure that glucose remains sufficiently low as to keep the yeast in respiration mode. In this manner, an ethanol facility may adhere to temperature, enzyme dosing and yeast inoculation guidelines without the need to monitor glucose levels in the reactor, or meter a glucose/molasses stream to the reactor.

Figure 3:
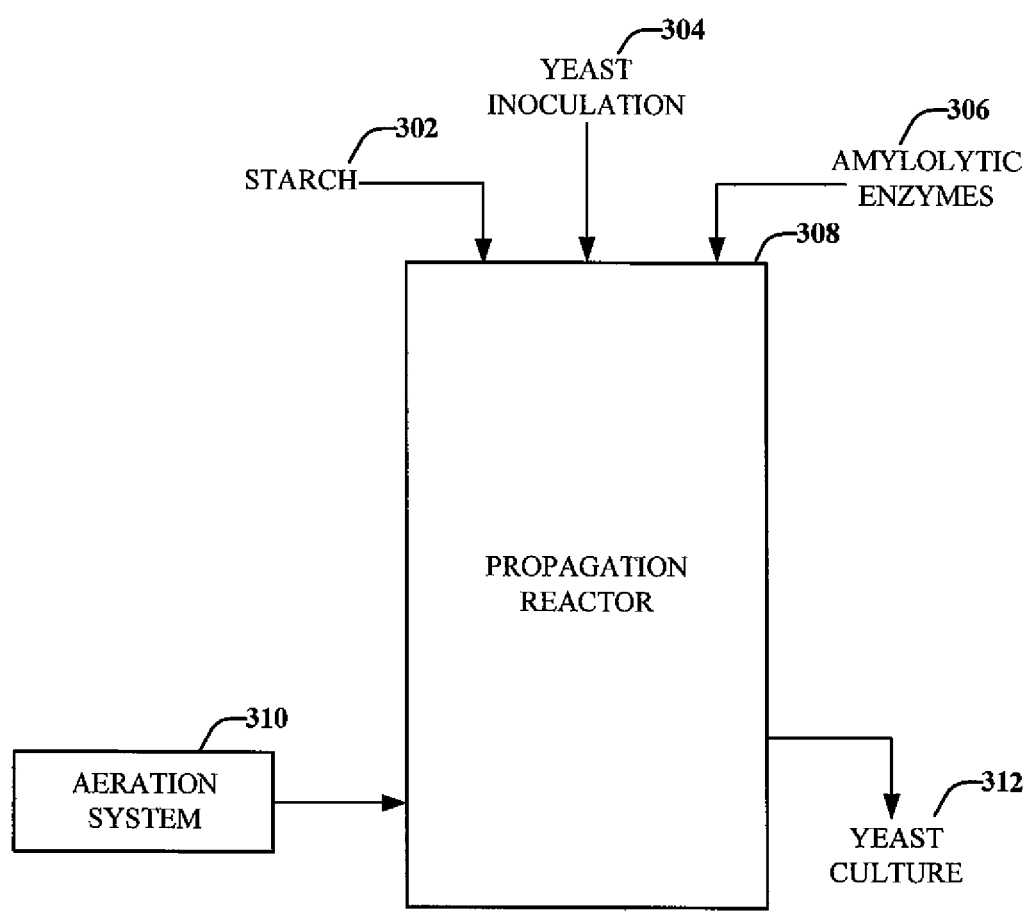
FIG. 3 shows an exemplary schematic block diagram of a propagation system according to the present invention.

An exemplary propagation system will now be described in connection with FIG. 3. As shown in FIG. 3, a feedstock material including starch stream 302 may be added to a propagation reactor 308, e.g., via a conveyor. Propagation reactors are well known and include stirred tanks as well as other reactors.

In addition to the starch 302, an initial inoculation 304 of yeast, and a dosage of amylolytic enzymes (an "enzyme cocktail") 306 are added. Optionally, one or more enzymes (e.g., the enzyme cocktail of amylolytic enzymes) may be added at a later stage after a lag phase of yeast growth has occurred. For example, a measurement system (not shown) can be used for adding the enzyme cocktail to the reactor 308. As described herein, the sugar (glucose) that is generated as the enzymes break down the starch functions as part of, or all of, a carbon source to propagate the yeast. Although not shown in FIG. 3, a nutrient source can be added to reactor 308, as well as any optional agents that are well known for use in a yeast propagation medium.

The yeast inoculum 304 is allowed to propagate in the reactor 308 for a set period of time under high oxygen concentrations. Oxygen can provided by an aeration system 310 which may sparge air through the reactor 308 and may also include mechanical agitation.

After propagation, the resulting yeast culture 312 can be collected and, e.g., delivered to downstream applications.

In some embodiments, propagation reactor 308 can be used within an ethanol production facility as described below with respect to FIGS. 1, 2A, and 2B for on-site propagation of yeast.

For example, after the propagation is complete, a yeast culture 312 may be removed from reactor 308 and supplied to fermentation such as fermentation system 222, or otherwise prepared for storage. In many cases, where the yeast are grown at the site of usage, the content of the propagator reactor 308 may be wholly supplied to fermentation. In other embodiments, it may be desirous to separate the yeast cells and/or wash the yeast from the propagation medium.

Figure 2A:
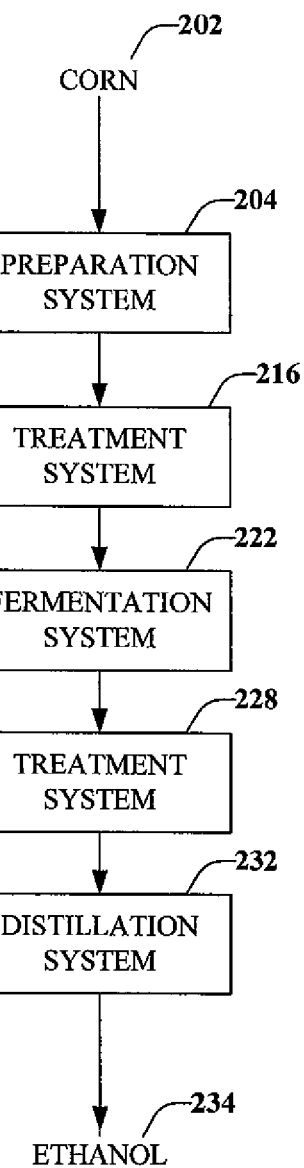
FIGS. 2A and 2B show exemplary process flow diagrams illustrating steps used to generate ethanol in a grain based ethanol production facility.
Figure 2B:
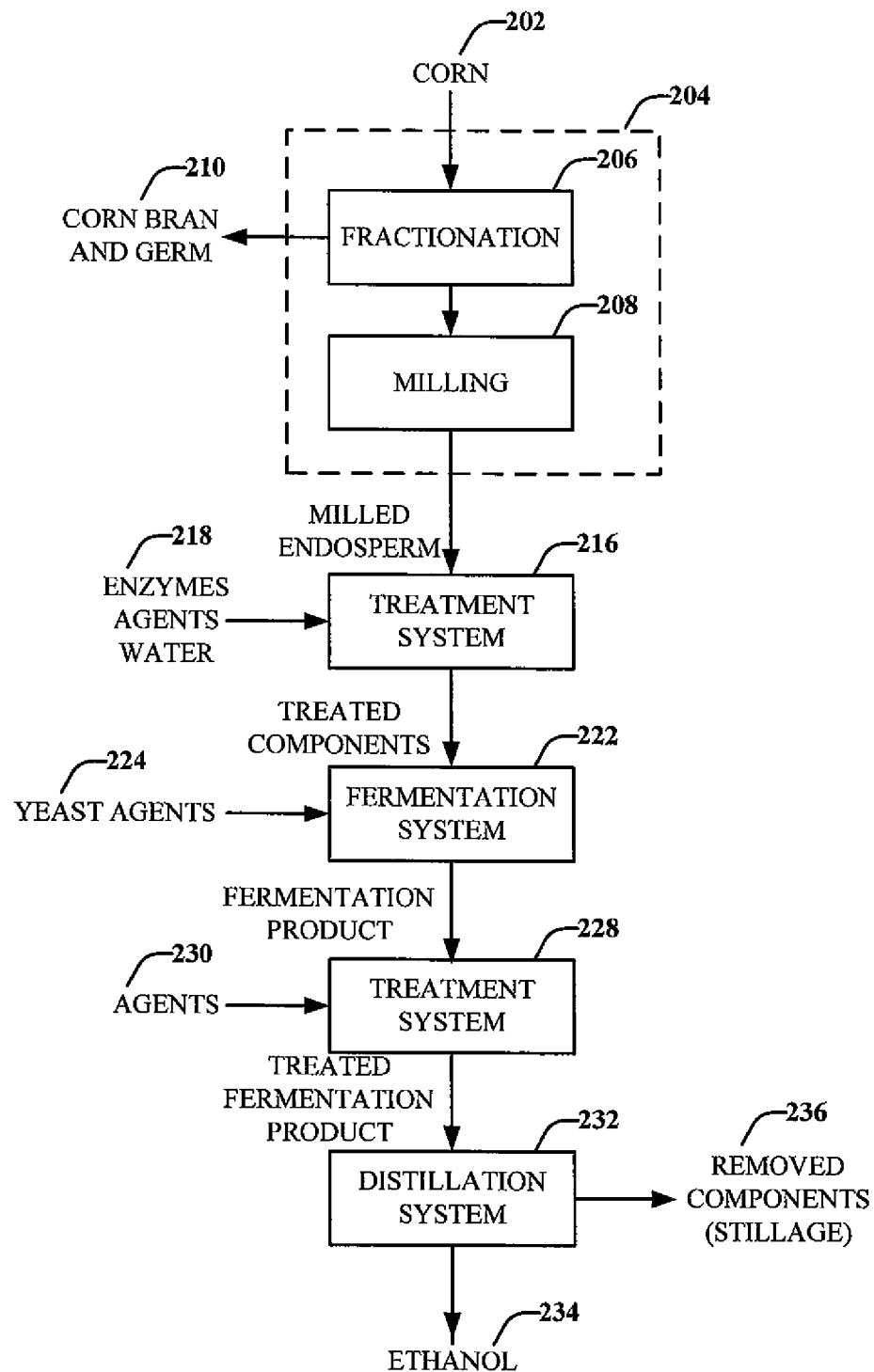

In order to illustrate how a propagation system according to the present invention can be used on-site at a ethanol production facility, FIGS. 1, 2A, and 2B will not be described. FIG. 1 is a perspective view of an exemplary biorefinery 100 including an ethanol production facility configured to produce ethanol from corn (or other starch source). The biorefinery 100 includes an area 102 where corn (or other suitable material including, but not limited to, biomass, sugars, and other starch products) is delivered and prepared to be supplied to the ethanol production facility. The ethanol production facility includes apparatus 104 for preparation and treatment (e.g., milling) of the corn into corn flour suitable for fermentation into fermentation product in a fermentation system 106. The ethanol production facility includes a distillation system 108 in which the fermentation product is distilled and dehydrated into ethanol. The biorefinery 100 may also include, in some embodiments, a by-product treatment system (e.g., a centrifuge, a dryer, and/or an evaporator).

In some embodiments, the biorefinery 100 may be referred to as a "fractionation" ethanol production facility, where the corn kernel, prior to milling, is fractionated into its three component parts. These include the outer shell (corn bran), which is predominantly a fiber material, the starch filled endosperm, and a protein rich germ portion. The benefit of fractionation is that the low starch components can be syphoned into different process streams if desired, thereby ensuring that only the high-starch endosperm undergoes liquefaction, fermentation and distillation. This provides an operation that can be more efficient, have lower yeast and enzyme requirements, and have lower energy expended per gallon of ethanol produced. Lastly, the corn bran and germ fractions may be sold as additional co-products for the feed industry, or may be further processed to generate higher value co-products.

While much of the discussion below is in connection with a whole kernel style biorefinery, it is considered within the scope of the present disclosure that fractionation plants may also be suitable facilities for including on-site yeast propagation as described herein. Additionally, as noted herein, any of the disclosed ethanol production facilities may include modifications for the processing of other feedstocks instead, or in addition to, corn kernels.

FIGS. 2A and 2B are exemplary process flow diagrams illustrating steps used to generate ethanol in an ethanol production facility. In an ethanol production process, corn 202 (or other suitable feed material) may be prepared for further treatment in a preparation system 204. As seen in FIG. 2B, the preparation system 204 may include a fractionation system 206 to fractionate the corn kernel into its three constituents, as described above. Fractionation may employ mills, size exclusion and density separation in order to be effectual. The bran and germ components 210 can be removed for further processing or sale as raw materials. In some cases, a screening process may be performed prior or post fractionation that removes foreign material, such as rocks, dirt, sand, pieces of corn cobs and stalk, and other unfermentable material (e.g., removed components).

After fractionation, the particle size of the endosperm may be reduced by milling 208 to facilitate further processing. The milled corn is slurried with water, enzymes and agents 218 to facilitate the conversion of starch into sugar (e.g. glucose), such as in a first treatment system 216. In "conventional" corn-to-ethanol facilities the flour slurry is typically heated in a jet cooker in order to convert the starch into sugar. By using an enzymatic approach, without any external heating, a "cold cook" process is achieved. Cold cooking benefits from a reduction in energy required, reduced overall costs, and minimal heat damage to the starch and proteins of the endosperm flour. Of course the propagation of yeast may be of benefit in a conventional ethanol facility involving a high heat cooking, as well as in cold-cook facilities.

The sugar (e.g., treated component) is converted into ethanol by an ethanologen (e.g. yeast or other agents 224) in a fermentation system 222. The yeast 224 can include yeast culture 312 from propagation reactor 308. Reactor 308 can be on-site or located at another facility of the ethanol manufacturer.

The product of fermentation (fermentation product) is typically referred to as "beer" and includes a liquid component, including ethanol and water and soluble components, and a solids component, including unfermented particulate matter (among other things). The fermentation product may optionally be treated with agents 230 in a second treatment system 228.

Yeast loading is typically optimized to ensure a reasonable fermentation time, mitigation of risk of lactic bacteria contamination, and yet as low a dosage as possible given the high cost of yeast given that it must be purchased from a supplier. In a facility that employs yeast propagation, initial loading levels may be dramatically increased (on the order of 10-100× loading levels) thereby providing dramatically shortened fermentations, very low risk of microbial contamination, and overall savings compared to purchasing yeast from a supplier.

In the illustrated standard facility, the treated fermentation product is sent to a distillation system 232. In the distillation system 232, the (treated) fermentation product is distilled and dehydrated into ethanol 234. In some embodiments, the removed components 236 (e.g., whole stillage), which comprise water, soluble components, oil and unfermented solids (e.g., the solids component of the beer with substantially all ethanol removed), may be dried into dried distillers grains (DDG) in a third treatment system (where the removed components may be treated with agents) and sold as an animal feed product. Other co-products, for example, syrup (and oil contained in the syrup), may also be recovered from the stillage.

EXAMPLES

The present invention will be further discussed by reference to the Examples below.

Example 1

The system similar to that as shown in FIG. 3 was used in an experiment to test the effectiveness of yeast propagation using starch slurry that is enzymatically treated. In this example, the *S. cerevisiae* strain was transferred from a YPD agar plate to 50 mL of sterile Yeast extract-Peptone (YP) media supplemented with 3% w/v glucose. The culture was grown at 30° C. overnight (approximately 17 hours) to reach an optical density at 600 nm of at least 7.5.

The growth medium for propagation has corn flour as the sole carbon source at 30 g/L (25.6 g dry/L) in conjunction with approximately 15 g/L clarified thin stillage and 0.24 g/L urea. Clarified thin stillage is the liquid phase resulting from the centrifugation of 7% total solid thin stillage at 4900×g for 20 minutes. This liquid layer is almost devoid of suspended solids.

The required amounts of clarified thin stillage, urea and water were added to the 5 L reactor and autoclaved at 110° C. for 6 min. Once cooled to 31.1° C., Lactoside247™ (commercially available from Lallemand Ethanol Technology, Milwaukee, Wis.) was added to 5 ppm final concentration to avoid bacterial contamination. This growth media was inoculated with the overnight yeast culture to get an inoculation rate of 0.1 g (dry yeast)/L. Just prior to inoculation of yeast, corn flour was added and the pH was adjusted to 5.0 using ammonium hydroxide or sulfuric acid. The reactor was agitated at 450 rpm, and airflow was regulated at 0.8 standard liters per minute (SLPM), (0.5 volumes of air per volume of medium per minute, vvm), to ensure adequate aeration.

The enzyme cocktail, including fungal alpha-amylase and fungal glucomylase) was added to 0.016 mL per g of corn solids (19 AGU/g DS; 1.8 FAU-F/g DS). The temperature of the reactor was maintained at 31.1° C. for the entire length of the study (24 hours). Samples were withdrawn periodically from the reactors and analyzed for growth, glucose consumption and ethanol production. The dissolved oxygen content and pH of the reactors were also monitored (not maintained).

Looking at Table 1 in FIG. 5A, it is clear that no ethanol was produced at the end of the 24 hour cycle. Further, all the glucose generated by the enzyme and the other components such as lactic acid, acetic acid and glycerol were all consumed by the yeast to produce yeast cell mass.

In this same study another reactor was included with just the growth media and the enzyme cocktail, but no yeast, just to observe the glucose production by the enzyme under the aerobic growth conditions. As is evidenced in Table 2 in FIG. 5B over 2% w/v glucose was produced.

Based on the glucose produced and the suspended solids present after 24 hours, it can be calculated that approximately 12 g dry yeast/L was produced during this propagation.

As can be seen, this study revealed that the strain tested produced more cell mass and no ethanol under highly aerated conditions. This suggested that yeast can be propagated even in starch-based medium with the appropriate amylolytic enzymes that release glucose slowly to avoid the Crabtree effect.

Example 2

In this second example, the findings of example 1 were confirmed using multiple yeast lines. The inoculum preparation and propagation procedures were the same as in example 1. However, in this study, two propagation reactors were set up: (i) genetically modified yeast; and (ii) non-genetically modified yeast. In both reactors, yeast was inoculated at 0.12 g/L.

Table 3 in FIG. 6A and Table 4 in FIG. 6B illustrate the results of this example study. The results obtained in this study suggested that this protocol can be used to propagate any number of *Saccharomyces cerevisiae* strains, both genetically modified and non-modified (wild-type). No ethanol production was observed in case of either of the strain.

Example 3

In this third example, a study was performed to confirm the concept of ethanol production on glucose and cell biomass production on starch based media. In this study, the corn solids were increased to 86 g dry corn solids/L (to achieve approximately 60 g/L glucose after hydrolysis of starch). The treatments included: (i) corn at 86 g/L, enzyme cocktail dose at 6.1 AGU/g dry solids and 0.6 FAU-F/g dry solids (added 3 hours after yeast inoculation), yeast at 0.12 g/L (Table 5); and (ii) Glucose at approximately 60 g/L, no enzyme, and yeast at 0.12 g/L (Table 6). The inoculum preparation and propagation protocols were similar to that used in example 1.

Table 6 in FIG. 7A and Table 7 in FIG. 7B indicate the results of these samples. The results were similar in terms of ethanol production. However, the uptake of other metabolites such as glycerol, lactic and acetic acids by the yeast indicates difference in growth patterns between the two substrates used. Ultimately, by optimizing enzyme dosage levels, the glucose content of the starch grown samples can remain low enough such that no ethanol is produced (as was seen in example 1). Enzyme dosage will vary as a function of starch loads, temperature, length of propagation, enzyme expressing strain(s), enzyme activity, starch source, and yeast strain. Further, it may be desirable, in some embodiments, to add higher levels of enzymes after a period of the propagation such that glucose production matches the increase in cells that are propagating.

Example 4

Figure 4:
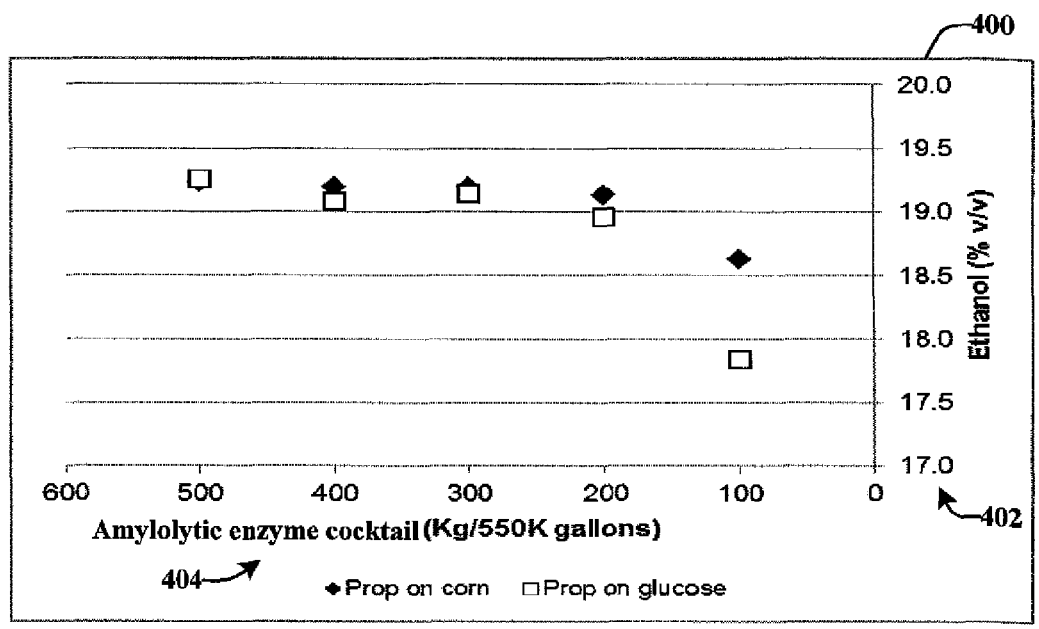
FIG. 4 shows a graph of ethanol produced under varying fermentation conditions according to Example 4.

In this example, a study was performed whereby the yeast cells grown in example 3 were used to inoculate a standard laboratory cold cook fermentation. By propagating the yeast strain in corn based medium and inoculating into the cold-cook fermentation, the exogenous saccharification enzyme dose in the fermentation can be reduced by 60%, as can be seen in relation to FIG. 4.

In this example graph 400, the enzyme loading level is indicated on the horizontal axis 404, and the ethanol yield is indicated on the vertical axis 402. At low enzyme dosages the yeast that was propagated on the starch medium performs substantially better than yeast grown on glucose. This indicates that some amylolytic enzymes were produced by the enzyme expressing genetically modified yeast strain during the propagation phase.

Example 5

In this example the protocol was modified to add the amylolytic enzymes after 3 hours of adding the yeast inoculum to the propagation reactor. This delayed addition of enzyme helps not to generate additional glucose before the yeast start growing. An optimized enzyme dose was also used. Yeast may be added in the active dry form or stabilized liquid cream form or from a frozen vial grown in the lab in sterile yeast extract, peptone medium supplemented with glucose. The propagation medium consisted of ground corn flour dosed at a level to give about 3% starch on dry weight basis in the reactor, thin stillage from corn ethanol biorefinery at 20 g dry solids/L. Urea was added at 0.24 g/L (~4 mM). Lactoside247™ (commercially available from Lallemand Ethanol Technology, Milwaukee, Wis.) was added to a final concentration of 5 ppm to prevent bacterial contamination. The pH of the medium was then adjusted to 5.0 using ammonium hydroxide. The temperature for propagation was set to 31.1° C. (88° F.). The contents were mixed well and yeast was inoculated at 0.1 g (dry yeast)/L. The air was turned on and the aeration was set to 1 volume air per volume medium per minute (vvm), and the agitation was set to 450 rpm. After 3 hours of yeast inoculation, the enzyme blend, BPX10.5 was added. The corresponding activities for fungal alpha amylase and glucoamylase based on the enzyme dosage used were 0.07 FAU-F/g dry solids and 0.74 AGU/g dry solids, respectively. The propagation was continued for 16 hours after which an approximate 100 fold increase in yeast mass was obtained. The sugars, organic acids, and ethanol after 16 h of aerobic yeast growth from duplicated experimental runs are shown in tables 7 and 8 below.

Sugars, Organic Acids and Ethanol after 16 h of Aerobic Yeast Growth in Starch Based Medium with Thin Stillage as Nutrient Source

TABLE 7

| Time (h) | Maltose (% w/v) | Glucose (% w/v) | Lactic acid (ppm) | Acetic acid (ppm) | Ethanol (% v/v) | Glycerol (% w/v) |
| --- | --- | --- | --- | --- | --- | --- |
| 0 | 0.069 | 0.138 | 426.779 | 147.631 | 0.058 | 0.291 |
| 3 | 0.019 | 0.047 | 431.82 | 162.749 | 0.154 | 0.298 |
| 16 | 0.01 | 0.016 | 35.382 | 9.664 | 0.04 | 0.139 |

TABLE 8

| Time (h) | Maltose (% w/v) | Glucose (% w/v) | Lactic acid (ppm) | Acetic acid (ppm) | Ethanol (% v/v) | Glycerol (% w/v) |
| --- | --- | --- | --- | --- | --- | --- |
| 0 | 0.067 | 0.137 | 426.747 | 147.831 | 0.058 | 0.289 |
| 3 | 0.018 | 0.045 | 427.024 | 162.981 | 0.154 | 0.296 |
| 16 | 0.013 | 0.011 | 25.804 | ND | 0.012 | 0.097 |

The embodiments as disclosed and described in the application (including the Figures and Examples) are intended to be illustrative and explanatory of the present invention. Modifications and variations of the disclosed embodiments, for example, of the apparatus and processes employed (or to be employed) as well as of the compositions and treatments used (or to be used), are possible; all such modifications and variations are intended to be within the scope of the present invention.

What is claimed is:

1. A method of propagating yeast comprising:
    (a) combining
        (i) a propagation medium comprising:
            a nutrient source;
        (ii) a carbon source comprising a starch feedstock material having one or more polysaccharides and/or one or more oligosaccharides;
        (iii) one or more amylolytic enzymes that can convert at least a portion of the one or more polysaccharides and/or one or more oligosaccharides into one or more monosaccharides; and
        (iv) a first cell mass of yeast, wherein the yeast can use at least a portion of the one or more monosaccharides to grow the first cell mass of the yeast for a time period to form a second cell mass of the yeast; and
    (b) enzymatically converting at least a portion of the one or more polysaccharides and/or one or more oligosaccharides into one or more monosaccharides at a temperature in the range from about 25 to 37° C.; and
    (c) growing the first cell mass of yeast on the propagation medium at a temperature in the range from about 25 to 37° C. for a time period to form the second cell mass of yeast that is greater in cell number than the first cell mass of yeast.

2. The method of claim 1, wherein the one or more enzymes are present in an amount and the one or more polysaccharides and/or one or more oligosaccharides are present in an amount so that substantially no ethanol is produced by the yeast during at least a portion of the time period.

3. The method of claim 2, wherein substantially no ethanol is produced by the yeast during the entire growing time period.

4. The method of claim 1, wherein the one or more enzymes are present in an amount and the one or more polysaccharides and/or one or more oligosaccharides are present in an amount to produce the one or more monosaccharides in an amount to grow the second cell mass of yeast within the time period.

5. The method of claim 4, wherein the one or more monosaccharides comprise glucose and wherein the amount of glucose produced within a 24 hour time period is less than 75 g/L.

6. The method of claim 1, further comprising providing the second cell mass of yeast to a fermentation process.

7. The method of claim 1, wherein the starch material comprises at least one of corn flour, milled corn endosperm, sorghum flour, soybean flour, wheat flour, biomass derived starch, and barley flour.

8. The method of claim 7, wherein the starch material is present in an amount in the range from 15 to 75 grams starch material per liter of the propagation medium.

9. The method of claim 1, wherein the first cell mass of yeast is provided to the propagation medium in an amount in the range from 0.02 to 5 grams dry yeast per liter of the propagation medium.

10. The method of claim 1, wherein the one or more enzymes comprise glucoamylase present in an amount in the range from 0.25 to 30 glucoamylase units (AGUs) per gram of dry solids in the propagation medium.

11. The method of claim 1, wherein the one or more enzymes comprise fungal alpha-amylase present in an amount in the range from 0.03 to 4 fungal alpha-amylase units (FAU-F) per gram of dry solids in the propagation medium.

12. The method of claim 1, wherein the one or more enzymes comprise 0.25 to 30 glucoamylase units (AGUs) per gram of dry solids in the propagation medium and approximately 0.03 to 4 fungal alpha-amylase units (FAU-F) per gram of dry solids in the propagation medium.

13. The method of claim 1, wherein the yeast comprises genetically modified *Saccharomyces cerevisiae* that can convert at least glucose and/or xylose to ethanol.

14. The method of claim 1, wherein the growing is performed for a time period in the range from 12 to 24 hours.

15. A system for propagating yeast comprising:
(a) a propagation reactor vessel, wherein the propagation vessel contains composition comprising:
 (i) a nutrient source;
 (ii) a carbon source comprising a starch feedstock material having one or more polysaccharides and/or one or more oligosaccharides;
 (iii) one or more amylolytic enzymes that can convert at least a portion of the one or more polysaccharides and/or one or more oligosaccharides into one or more monosaccharides at a temperature in the range from about 25 to 37° C.; and
 (iv) a first cell mass of yeast, wherein the yeast can use at least a portion of the one or more monosaccharides as a feed source;
wherein the propagation reactor vessel is configured for enzymatic hydrolysis of the starch feedstock material, and for growth of the first cell mass of yeast at a temperature in the range from about 25 to 37° C. to form a second cell mass of the yeast; and
(b) an aerator coupled to the propagation reactor vessel.

* * * * *

UNITED STATES PATENT AND TRADEMARK OFFICE
CERTIFICATE OF CORRECTION

| | |
|---|---|
| PATENT NO. | : 9,034,631 B2 |
| APPLICATION NO. | : 13/804364 |
| DATED | : May 19, 2015 |
| INVENTOR(S) | : Neelakantam V. Narendranath and Stephen M. Lewis |

It is certified that error appears in the above-identified patent and that said Letters Patent is hereby corrected as shown below:

In the Claims

Claim 2, Column 12, Line 40, "enzymes are present in an amount and the one or more" should be
– amylolytic enzymes are present in an amount and the one or more –

Claim 4, Column 12, Line 49, "enzymes are present in an amount and the one or more" should be
– amylolytic enzymes are present in an amount and the one or more –

Claim 10, Column 13, Line 6, "enzymes comprise glucoamylase present in an amount in the" should
be – amylolytic enzymes comprise glucoamylase present in an amount in the –

Claim 11, Column 13, Line 10, "enzymes comprise fungal alpha-amylase present in an" should be
– amylolytic enzymes comprise fungal alpha-amylase present in an –

Claim 12, Column 13, Line 14, "enzymes comprise 0.25 to 30 glucoamylase units (AGUs) per" should
be – amylolytic enzymes comprise 0.25 to 30 glucoamylase units (AGUs) per –

Signed and Sealed this
Sixteenth Day of August, 2022

*Katherine Kelly Vidal*

Katherine Kelly Vidal
*Director of the United States Patent and Trademark Office*